US012751632B2

(12) United States Patent
Kilbaugh et al.

(10) Patent No.: US 12,751,632 B2
(45) Date of Patent: Oct. 6, 2026

(54) NON-INVASIVE CEREBRAL MONITORING AND CEREBRAL METRIC-BASED GUIDANCE FOR MEDICAL PROCEDURES

(71) Applicants: The Children's Hospital of Philadelphia, Philadelphia, PA (US); The Trustees of the University of Pennsylvania, Philadelphia, PA (US)

(72) Inventors: Todd Kilbaugh, Philadelphia, PA (US); Tiffany Ko, Philadelphia, PA (US); Constantine Mavroudis, Philadelphia, PA (US); Daniel Licht, Philadelphia, PA (US); Arjun Yodh, Merion, PA (US); Robert Berg, Merion, PA (US); Ryan Morgan, Philadelphia, PA (US); Robert Sutton, Garnet Valley, PA (US); Wesley Baker, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 1109 days.

(21) Appl. No.: 17/772,606

(22) PCT Filed: Nov. 4, 2020

(86) PCT No.: PCT/US2020/058809
§ 371 (c)(1),
(2) Date: Apr. 28, 2022

(87) PCT Pub. No.: WO2021/091961
PCT Pub. Date: May 14, 2021

(65) Prior Publication Data

US 2023/0000362 A1 Jan. 5, 2023

Related U.S. Application Data

(60) Provisional application No. 62/965,220, filed on Jan. 24, 2020, provisional application No. 62/930,699, filed on Nov. 5, 2019.

(51) Int. Cl.
*A61B 5/0205* (2006.01)
*A61B 5/024* (2006.01)
*A61B 5/1455* (2006.01)

(52) U.S. Cl.
CPC ............ *A61B 5/0205* (2013.01); *A61B 5/024* (2013.01); *A61B 5/14551* (2013.01)

(58) Field of Classification Search
None
See application file for complete search history.

(56) References Cited

U.S. PATENT DOCUMENTS 5,579,774 A 12/1996 Miller et al.
6,802,812 B1 10/2004 Walker et al.
(Continued)

FOREIGN PATENT DOCUMENTS

CN 103654760 B 8/2016
WO 2021091961 A1 5/2021

OTHER PUBLICATIONS

Richard M. Odell et al., "Use of pulse oximetry to monitor venous saturation during extracorporeal life support", Critical Care Medicine, vol. 22, No. 4, 1994 (Year: 1994).*
(Continued)

*Primary Examiner* — Dmitry Suhol
*Assistant Examiner* — Alyssa N Biancamano
(74) *Attorney, Agent, or Firm* — Buchanan Ingersoll & Rooney PC

(57) ABSTRACT

A cardiopulmonary resuscitation (CPR) cerebral monitoring device including a measurement probe having one or more optical emitters, and one or more optical detectors, and including an optical instrument having an optical source, and an optical detector. Also included is a controller configured to control the optical instrument to emit multispectral light through the one or more optical emitters to
(Continued)

200 illuminate a tissue, control the optical detector to detect multi-spectral light emitted from the illuminated tissue, compare the emitted multi-spectral light to the detected multi-spectral light, compute a plurality of cerebral tissue parameters based on the comparison, determine CPR procedures based on the plurality of cerebral tissue parameters, and control a user output device to instruct a user to perform the CPR procedures, and/or control an automated CPR device to perform the CPR procedures.

8 Claims, 9 Drawing Sheets

(56) References Cited

U.S. PATENT DOCUMENTS

| | | | | |
|---|---|---|---|---|
| 7,104,958 | B2 | 9/2006 | Crutchfield et al. | |
| 8,965,472 | B2 * | 2/2015 | Benni | A61B 5/14553 600/323 |
| 2005/0065556 | A1 * | 3/2005 | Reghabi | A61B 5/14546 607/5 |
| 2008/0125821 | A1 * | 5/2008 | Blomquist | A61N 1/39044 601/41 |
| 2011/0105912 | A1 * | 5/2011 | Widman | A61B 5/4076 600/483 |
| 2015/0105636 | A1 | 4/2015 | Hayman et al. | |
| 2016/0058395 | A1 | 3/2016 | Muser et al. | |
| 2016/0256130 | A1 | 9/2016 | Hamilton et al. | |
| 2017/0095601 | A1 | 4/2017 | Laubscher et al. | |
| 2017/0105671 | A1 * | 4/2017 | Borgos | A61B 5/6814 |
| 2018/0103861 | A1 | 4/2018 | Sutin et al. | |
| 2018/0133103 | A1 | 5/2018 | Lurie | |
| 2018/0303391 | A1 | 10/2018 | Roblyer et al. | |
| 2018/0303411 | A1 | 10/2018 | Walker et al. | |
| 2019/0254584 | A1 | 8/2019 | Atlas et al. | |
| 2020/0000680 | A1 * | 1/2020 | Silver | A61H 31/00 |
| 2021/0350927 | A1 * | 11/2021 | Kvernebo | G16H 50/20 |
| 2022/0361764 | A1 | 11/2022 | Sutin et al. | |
| 2022/0409080 | A1 | 12/2022 | Kyriacou et al. | |

OTHER PUBLICATIONS

International Preliminary Report on Patentability and Written Opinion for International Application No. PCT/US2020/058809, issued May 10, 2022, 10 pages.

Elwishi et al., "Monitoring the Brain", BJA Education, (Nov. 2, 2019), vol. 19, No. 2, pp. 54-59.

Notification of Transmittal of the International Search Report (Forms PCT/ISA/220 and PCT/ISA/210) and the Written Opinion of the International Searching Authority (Form PCT/ISA/237) issued Sep. 19, 2024, by the Commissioner for Patents in corresponding International Application No. PCT/US2024/035219. (13 pages).

International Search Report and Written Opinion issued in PCT/US2020/058809, mailed Feb. 1, 2021, 10 pages.

International Search Report and Written Opinion for International Application No. PCT/US2022/047215, mailed Jan. 27, 2023, 11 pages.

* cited by examiner

400

NON-INVASIVE CEREBRAL MONITORING AND CEREBRAL METRIC-BASED GUIDANCE FOR MEDICAL PROCEDURES

CROSS-REFERENCE TO RELATED APPLICATIONS

This is a U.S. National Phase Application of PCT International Patent Application No. PCT/US2020/058809, filed Nov. 4, 2020, which claims priority to U.S. Provisional Patent Application No. 62/930,699, filed Nov. 5, 2019, entitled "NON-INVASIVE CEREBRAL MONITORING AND CEREBRAL METRIC-BASED GUIDANCE FOR MEDICAL PROCEDURES" and U.S. Provisional Patent Application No. 62/965,220, filed Jan. 24, 2020, entitled "NON-INVASIVE CEREBRAL MONITORING AND CEREBRAL METRIC-BASED GUIDANCE FOR MEDICAL PROCEDURES", the contents of which are incorporated herein by reference in their entirety.

FIELD

The subject matter disclosed herein relates to devices, systems and methods for providing non-invasive cerebral monitoring and cerebral metric-based guidance for medical procedures.

BACKGROUND

Each year, about 500,000 people suffer from a Cardiac Arrest in the United States. Cardiac Arrest is highly lethal resulting in more than 250,000 deaths each year in the United States. Typical treatment for Cardiac Arrest includes cardiopulmonary resuscitation (CPR), potentially followed by extracorporeal life support (ECLS) if necessary. While CPR and ECLS improve initial survival, many patients do not survive to hospital discharge, and those that do survive often have significant neurologic impairment. A major impediment to developing and improving neuroprotective strategies in patients who are suffering from, or recovering from, a Cardiac Arrest is that there is no efficient way to guide and control CPR, ECLS, or any other medical procedure to minimize neurologic impairment due to Cardiac Arrest.

SUMMARY

An embodiment includes a cardiopulmonary resuscitation (CPR) cerebral monitoring device comprising a measurement probe including one or more optical emitters and one or more optical detectors, an optical instrument including an optical source and an optical detector, and a controller. The controller is configured to control the optical instrument to emit multi-spectral light through the one or more optical emitters to illuminate a tissue, control the optical detector to detect multi-spectral light emitted from the illuminated tissue, compare the emitted multi-spectral light to the detected multi-spectral light, compute a plurality of cerebral tissue parameters based on the comparison, determine CPR procedures based on the plurality of cerebral tissue parameters, and control a user output device to instruct a user to perform the CPR procedures, and/or control an automated CPR device to perform the CPR procedures.

An embodiment includes an extracorporeal life support (ECLS) cerebral monitoring device comprising a measurement probe including one or more optical emitters and one or more optical detectors, an optical instrument including an optical source and an optical detector, and a controller. The controller is configured to control the optical instrument to emit multi-spectral light through the one or more optical emitters to illuminate a tissue, control the optical detector to detect multi-spectral light emitted from the illuminated tissue, compare the emitted multi-spectral light to the detected multi-spectral light, compute a plurality of cerebral tissue parameters based on the comparison, determine ECLS procedures based on the plurality of cerebral tissue parameters, and control a user output device to instruct a user to perform the ECLS procedures, and/or control an automated ECLS device to perform the ECLS procedures.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Introduction

The following description describes systems and methods for guiding medical personnel and/or controlling medical devices to perform and/or adjust medical procedures based on cerebral tissue parameters. Specifically, a non-invasive device that monitors brain oxygen levels is incorporated into lifesaving medical equipment that ensures that patients receive treatment to maximize their brain oxygen levels, thus maximizing their quality of life upon recovery. Real-time measurements of cerebral blood flow and cerebral oxygen saturations are taken, and a graphical-user interface outputs medical instructions and/or oxygen levels such as oxygen balance, oxygen saturation, etc. to caregivers. These oxygen levels may be used to automatically control medical equipment such as CPR compression bands, defibrillators and ECLS circulatory pumps, or displayed on the graphical user interface to help caregivers manually determine how to adjust treatment when performing CPR and ECLS, and when to switch from CPR to ECLS.

Figure 1:
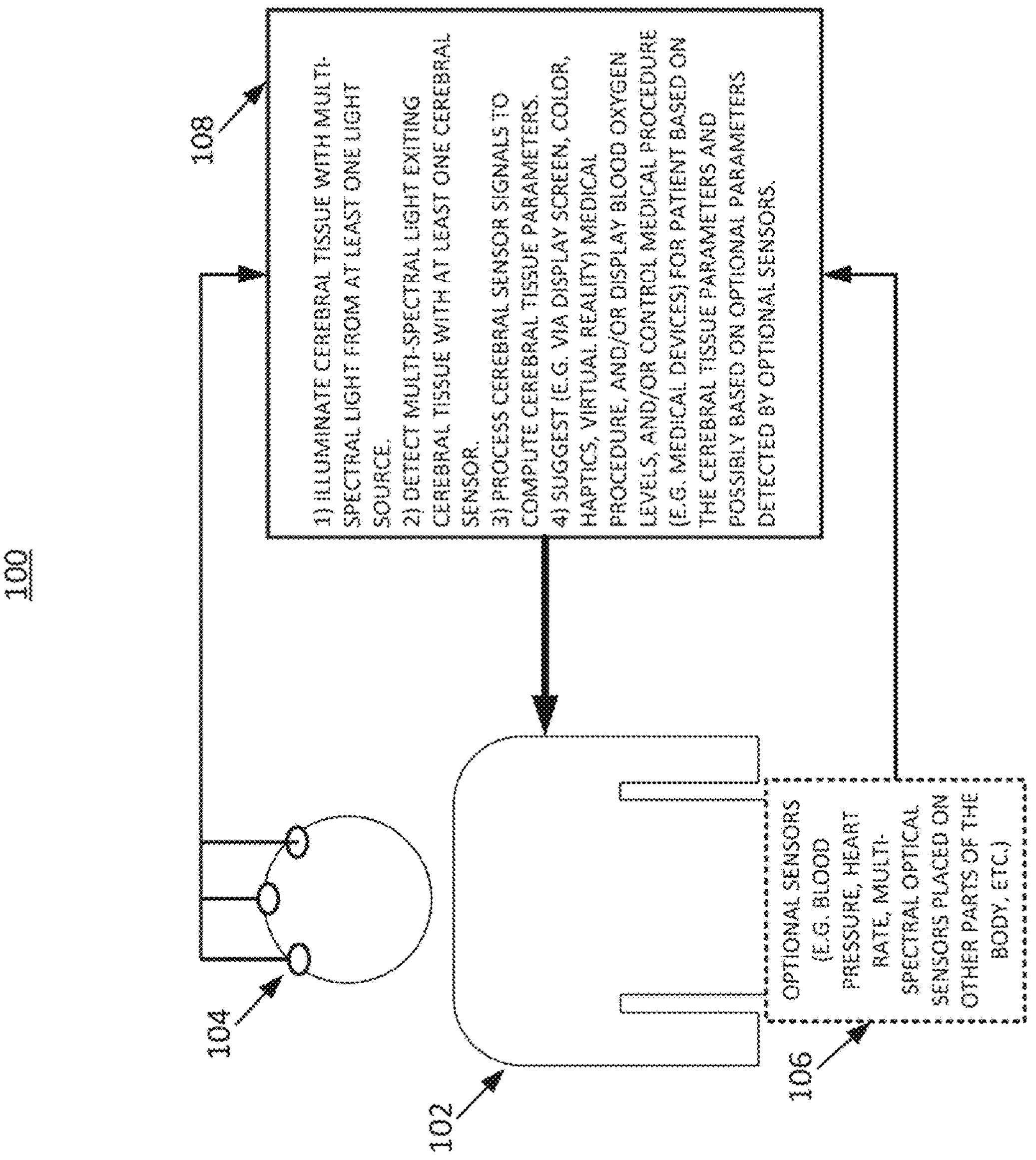
FIG. 1 is a view of an operational flow for medical procedure guidance/control, based on cerebral monitoring according to an aspect of the disclosure.

FIG. 1 is an example of an operational flow 100 for medical procedure guidance/control based on cerebral monitoring. In FIG. 1, for example, patient 102 may be in a state of cardiac arrest. Optical measurement probes 104, and optional sensors 106 (e.g. blood pressure, peripheral blood flow (including carotid blood flow), heart rate, optical measurement probes positioned on other parts of the body (carotid, heart, arms, legs, etc.)) are attached to patient 102 by a caregiver (not shown). In one example, system 108 includes a controller, user input/output and optional automated medical sensors and devices. System 108 controls optical measurement probes 104 (e.g. attached to the scalp of patient 102) to illuminate cerebral tissue with light (e.g. multi-spectral light) from at least one light source, and then detect light exiting the cerebral tissue with at least one optical detector. Each optical measurement probe 104 includes of at least one emitter-detector pair. System 108 then analyzes cerebral monitoring signals received from optical measurement probes 104 to compute cerebral tissue parameters (e.g. optical absorption, optical scattering, blood flow, tissue oxygenation, hemoglobin concentration and cerebral metabolism).

System 108 may also analyze monitoring signals from optional sensors to determine other parameters. As described above, these optional sensors may include blood pressure sensors, heart rate sensors, etc. These optional sensors may also include additional optical measurement (e.g. the same as optical measurement probes 104) that are attached to other parts of the body such as the carotid, heart, arms and legs to measure peripheral blood flow. In one example, system 108 may control these other optical measurement probes to illuminate tissue of these other parts of the body with light (e.g. multi-spectral light) from at least one light source, and then detect light exiting the tissue of these other parts of the body with at least one optical detector. System 108 may then analyze these optional tissue monitoring signals received from the other optical measurement probes to compute optional tissue parameters for the other parts of the body (e.g. optical absorption, optical scattering, blood flow, tissue oxygenation, hemoglobin concentration, etc.).

In one scenario, system 108 instructs the caregiver via user input/output (e.g. via display screen, color, haptics, virtual reality) to perform/adjust medical procedures (e.g. manual CPR procedures such as chest compressions) for treating the patient based on the cerebral tissue parameters, based on optional parameters detected by optional sensors 106, and based on optional patient information (e.g. medical history, age, weight, systemic hemodynamics, other organ optical measurements, etc.). In another scenario, system 108 controls automated medical devices (e.g. automated CPR device) to perform/adjust medical procedures or medications (e.g. automated CPR procedures such as chest compressions, medication delivery) for treating the patient based on the cerebral tissue parameters, based on optional parameters detected by optional sensors 106, and based on optional patient information (e.g. medical history, age, weight, systemic hemodynamics, other organ optical measurements, etc.).

In a third scenario, system 108 can both instruct the caregiver and control the automated medical devices. For example, system 108 can control the automated CPR device to perform chest compressions, while instructing the caregiver via user input/output to administer medication. In some embodiments, instructions output by the user output device can include at least one of administration of medication and alteration of anesthesia.

For a manual CPR scenario, for example, the medical procedures could include user instructions for chest compression depth/rate, air flow rate/volume/composition and any other procedure utilized during manual CPR. For an automated CPR scenario, the medical procedures could be the automated control of a chest compression device, artificial lung, artificial heart or pump, or any other device utilized during automated CPR.

Although CPR is described above, it is noted that the system could be used for instructing the user (e.g. the caregiver) or controlling automated devices for assisting in other medical procedures/treatments including, but not limited to ECLS of a patient or any medical procedures/treatments where cerebral tissue parameters are important to preventing/minimizing neurological damage.

Device Hardware

Figure 2A:
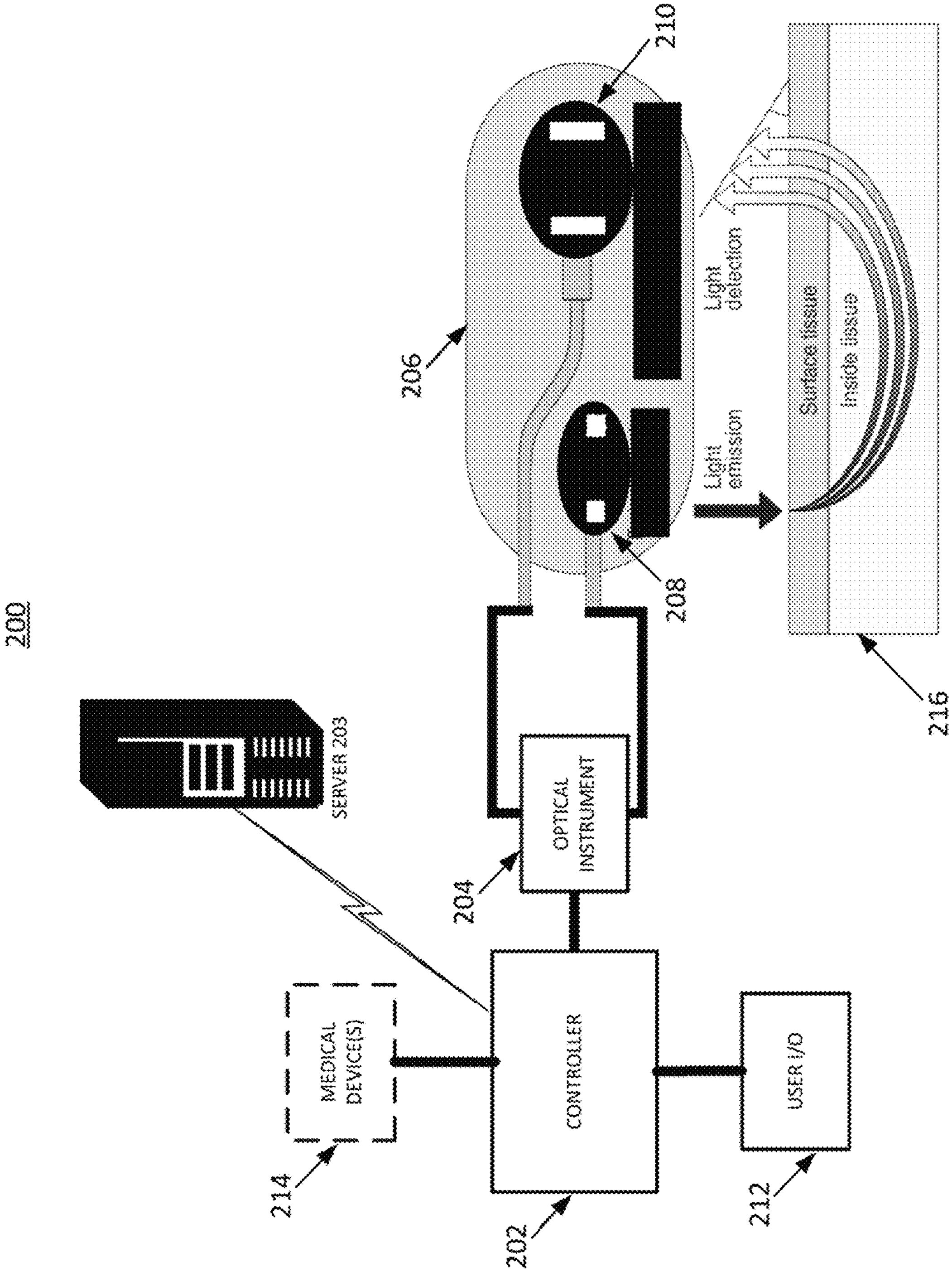
FIG. 2A is a view of a control system for medical procedure guidance/control, based on cerebral monitoring according to an aspect of the disclosure.

FIG. 2A is a view of a control system 200 for implementing the medical procedure guidance/control based on cerebral monitoring described in FIG. 1. In this example, control system 200 includes at least one optical measurement probe 206 having one or more optical emitters 208 and one or more optical detectors 210 for illuminating and detecting light, respectively, in tissue 216 (e.g. cerebral tissue), and optical instrument 204 for providing/receiving the light to/from the optical emitters 208 and optical detectors 210. Also included is user (e.g. caregiver) input/output (I/O) device(s) 212, optional medical device(s) 214, controller 202 for controlling the system and optional server 203 for updating software programs and data stored on controller 202.

Figure 2B:
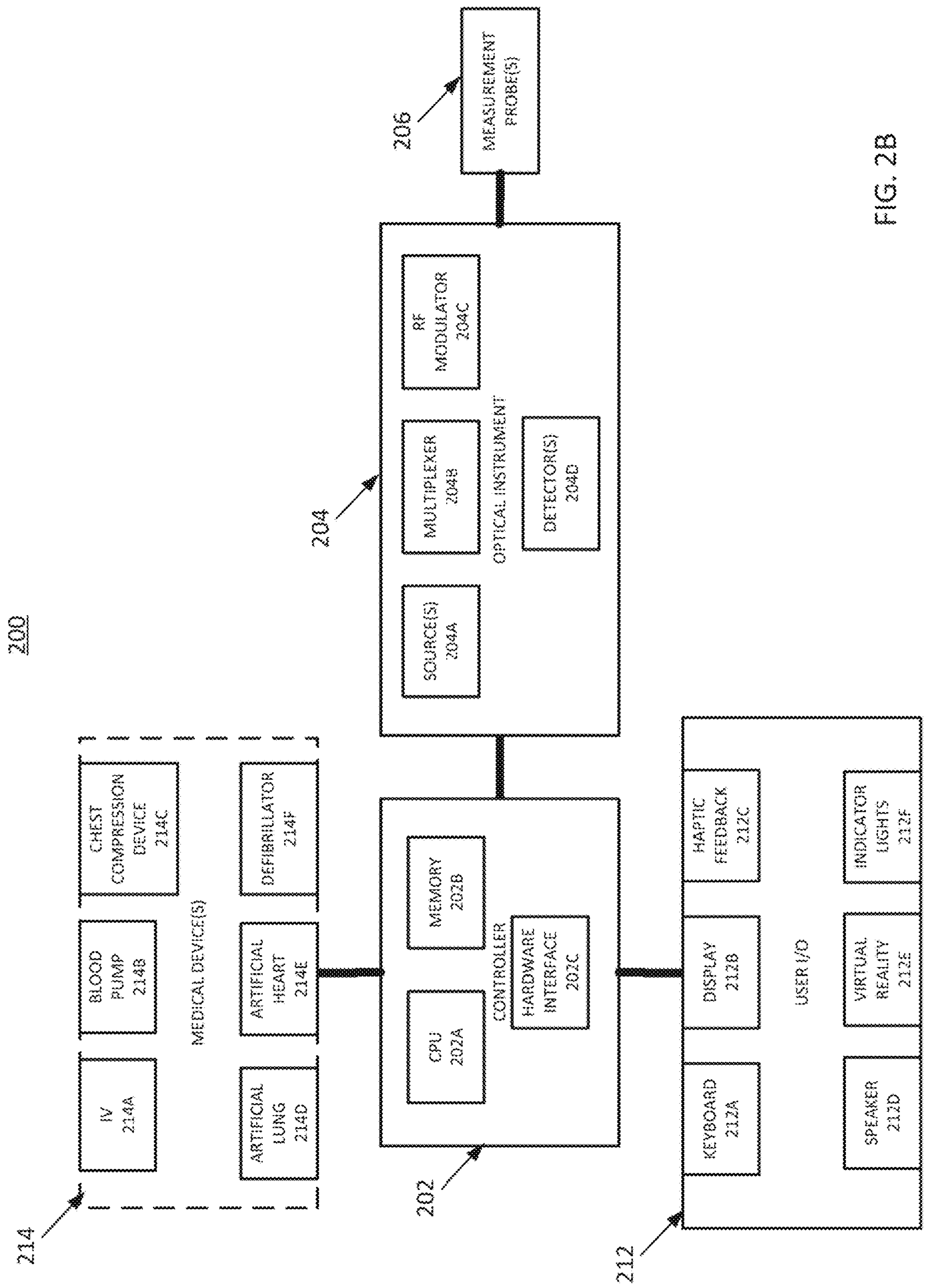
FIG. 2B is a detailed view of the control system for medical procedure guidance/control, based on cerebral monitoring shown in FIG. 2A, according to an aspect of the disclosure.

Further details of example control system 200 are shown in FIG. 2B. In this example, controller 202 includes a central processing unit (CPU) 202A for processing data, memory 202B for storing data and software programs and hardware interface 202C for interfacing CPU 202A to the other hardware devices in the system. Optical instrument 204 includes one or more optical sources 204A (e.g. lasers of different wavelengths or a multispectral light source) for outputting multi-spectral light to measurement probes 206 (e.g. via optical fiber), optical multiplexer 204B for time division multiplexing of optical sources 204A (e.g. multiplexing the lasers of different wavelengths to produce multispectral light), radio frequency (RF) optical modulator 204C for optically modulating the multiplexed optical sources to RF frequencies, and then outputting light to measurement probes 206, and one or more optical detectors 204D (e.g. photodiodes) for detecting the light detected by measurement probes 206.

The power, coherence, number and emission wavelengths of optical sources 204A are set based on various factors including optical measurement technique (e.g., frequency-domain versus time-domain diffuse optical spectroscopy), required measurement time resolution, the anatomical region of measurement, and cerebral tissue parameters that are of importance for the particular medical procedure/treatment being implemented. In addition, the number and positioning of optical emitters 208 and optical detectors 210 are also set based on these factors.

For example, the optical instrument 204 in the system may include eight optical sources 204A (e.g. lasers), comprising two duplicated sets of four unique near-infrared wavelengths (multi-spectral), and the measurement probes 206 may each include two optical emitters 208 spaced at various distances from a single optical detector 210. In operation, CPU 202A controls multiplexer 204B to sequentially output each of the first set of four lasers from the first optical emitter, followed by sequentially outputting each of the second set of the four lasers from the second optical emitter. This produces 8 independent emissions and detections of the laser light through the cerebral tissue which is then analyzed by CPU 202A to determine the cerebral tissue parameters.

In addition, the system also includes user I/O 212 having one or more of keyboard 212A, display 212B, haptic feedback device 212C, speaker 212D, virtual reality device 212E and indicator lights 212F for receiving input (e.g. patient information) and providing output (e.g. output on at least one of display 212B, haptic feedback device 212C, speaker 212D, virtual reality device 212E and indicator lights 212F, medical procedure instructions, and/or a graph or numerical values of blood oxygen levels such as blood oxygen balance, blood oxygen saturation, blood oxygen content, or any other blood oxygen measure) to the caregiver. In addition, optional medical devices 214 include one or more of IV pump device 214A, blood pump 214B, chest compression device 214C, artificial lung 214D, artificial heart 214E and defibrillator 214F. Other medical devices may also be included depending on the medical procedure/treatment in which the system is assisting.

Operational Overview and Signal Processing

Figure 3:
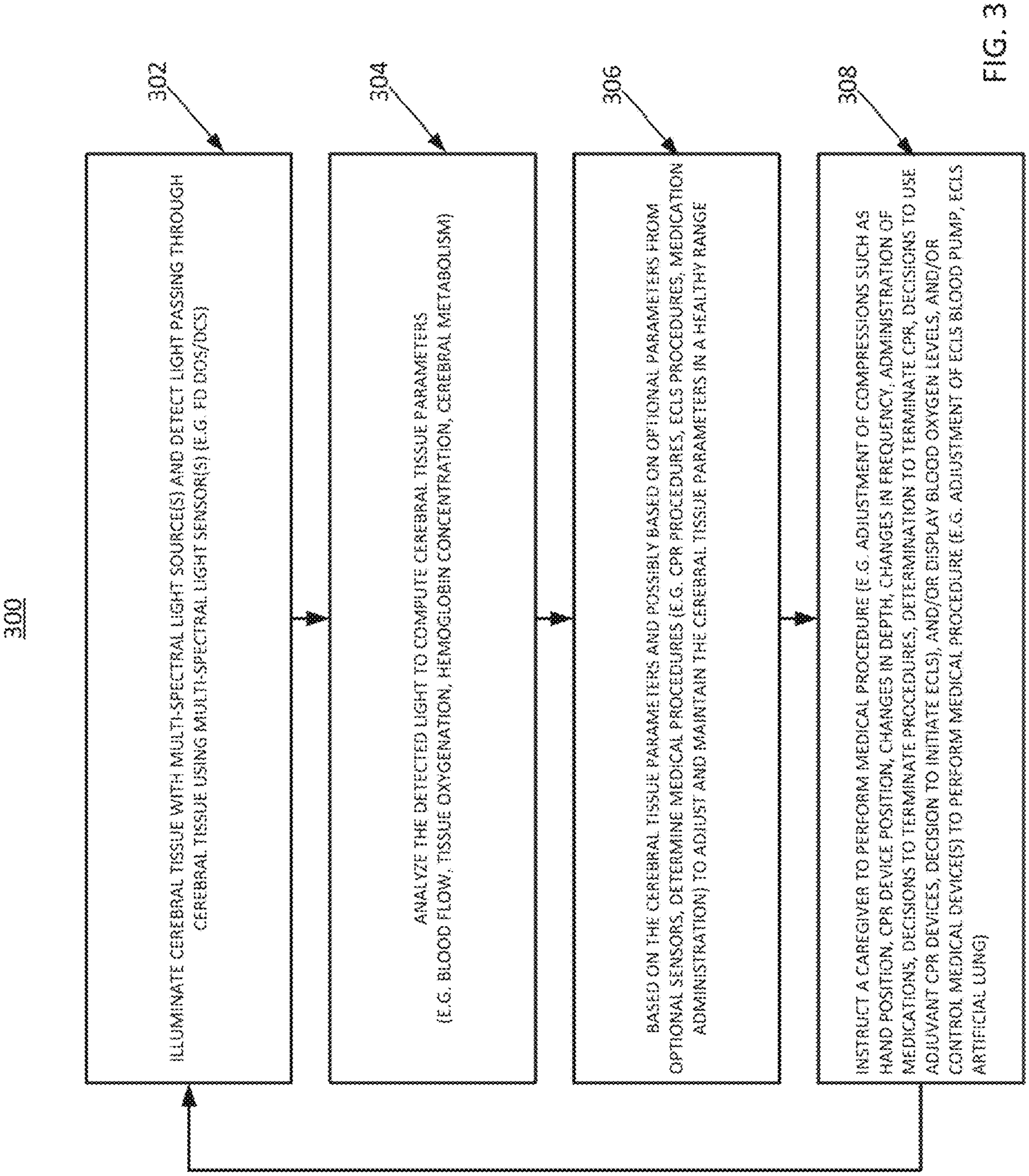
FIG. 3 is a flowchart for the operational flow shown in FIG. 1, according to an aspect of the disclosure.

FIG. 3 is a flowchart 300 describing the operational flow shown in FIG. 1 using control system 200 shown in FIGS. 2A and 2B. In step 302, CPU 202A of controller 202 executes a computer program stored in memory 202B. The computer program instructs CPU 202A to control the optical instrument 204 to illuminate the tissue 216 (e.g. cerebral tissue) of patient 102 with light (e.g. multi-spectral light) via optical emitters 208, and to detect light passing through tissue 216 (e.g. cerebral tissue) via optical detectors 210. In one example, CPU 202A may control optical multiplexer 204B to perform time division multiplexing to sequentially drive the source lasers' 204A output (each for a period of time T, each with specific emission wavelength), which are amplitude modulated using RF optical modulator 204C onto an RF optical carrier (e.g. 110 MHz), for transmission of light to optical emitters 208, each with a specific position on an optical probe 206. In step 304, the light detected at optical detector positions 210 and transmitted to optical detector(s) 204D is then analyzed by CPU 202A to compute cerebral tissue parameters, which include but are not limited to optical scattering and absorption properties ($\mu_s'$ and $\mu_a$, respectively), blood flow, tissue oxygenation, hemoglobin concentration and cerebral metabolism. More specifically, steps 302 and 304 may include a combination of frequency domain diffuse optical spectroscopy (FD-DOS) and diffuse correlation spectroscopy (DCS) referred to herein as FD-DOS/DCS to dictate light emission and detection schema (e.g. optical instrument 204 and measurement probe 206), analyze the light signals and compute the cerebral tissue parameters. FD-DOS uses RF amplitude modulated laser sources to quantify both optical scattering and optical absorption in the tissue which is beneficial to more accurately determine the cerebral tissue parameters, as compared to optical instruments where RF modulation and resulting phase information is not used. More generally, any optical instrument 204 and measurement probe 206 configuration which is able to quantify optical scattering and optical absorption at multiple wavelengths may be used in place of FD-DOS. Similarly, any optical instrument 204 and measurement probe 206 configuration which permits optical measurement of cerebral blood flow may be used in place of DCS.

Alternatively, steps 302 and 304 may include a combination of time domain diffuse optical spectroscopy (TD-DOS) and DCS. Further details of hybrid diffuse reflectance spectroscopy techniques, FD-DOS/DCS, TD-DOS/DCS, alternative optical instruments and probe configurations can be found in U.S. Pat. No. 8,082,015 which is incorporated herein by reference.

Based on the cerebral tissue parameters determined in step 304, and possibly based on optional parameters determined from optional sensors 106 and optional patient information input via user I/O 212 and CPU 202A, in step 306 CPU 202A then determines beneficial adjustments to medical procedures (e.g. manual/automatic procedures such as CPR procedures, ECLS procedures, medication administration, etc.) in order to maintain the cerebral tissue parameters in a healthy range. CPU 202A makes this determination based on a predetermined table of medical procedures that are associated with certain cerebral tissue parameters, or based on an algorithm that computes which medical procedures should be adjusted and how they should be adjusted to achieve the desired results. Alternatively, the caregiver may determine the beneficial adjustments to the medical procedures based on an analysis of the cerebral tissue parameters, the optional parameters, the optional patient information input, professional experience and other factors.

The predetermined table, for example, includes a healthy range and an unhealthy range of each cerebral tissue parameter, or for combinations of cerebral tissue parameters. The healthy ranges may then be associated with specific adjustments of medical procedures that are predetermined to maintain the cerebral tissue parameters in the healthy ranges. Likewise, the unhealthy ranges may then be associated with specific adjustments of medical procedures that are predetermined to drive the cerebral tissue parameters out of the unhealthy ranges and into the healthy ranges. Controller 200 compares the measured cerebral tissue parameters to the cerebral tissue parameters in the table to find a match, and then adjusts the medical devices and/or instructions based on the associated adjustment values. The healthy ranges, unhealthy ranges and associated medical procedure adjustments in the table may be predetermined based on medical research.

The algorithm, for example, may include an adaptive filter that learns from the success (or lack of success) of prior attempts to drive and maintain the cerebral tissue parameters into the healthy range. Such an algorithm can be initialized based on medical research and then optimized over time. This would also allow for the system to adapt and be optimized to a particular patient.

In one example, the predetermined table or the algorithm described above may be executed locally by controller 200. In this example, the predetermined table or the algorithm may be updated locally by a memory device (e.g. flash drive) or remotely from optional server 203 via a wireless communication link (e.g. WiFi, Cellular, etc.).

In another example, the predetermined table or the algorithm described above may be stored and executed remotely by server 203. In this example, controller 200 would send the measured data to optional server 203 which would then analyze the data, compute the cerebral parameters and transmit appropriate instructions (e.g. medical procedure adjustments) back to controller 200 for execution. This would reduce the processing burden on controller 200.

Optional server 203 may be used to store and update the predetermined table or the algorithm based on the latest medical research and results. Controller 200, as well as other controllers for other medical devices may then download the latest predetermined table or the algorithm to increase accuracy of patient monitoring and treatment.

In step 308, CPU 202A then: 1) instructs a caregiver (e.g. medical professional) via one or more of display 212B, haptic feedback device 212C, speaker 212D, virtual reality device 212E or indicator lights 212F to adjust or execute the determined medical procedure (e.g. adjustment of chest compressions such as hand position, automated CPR device positioning, changes in compression depth, changes in compression frequency, administration of medications, decisions to terminate procedures, decision to initiate ECLS), and/or 2) displays blood oxygen levels, and/or 3) controls automated medical device(s) including one or more of IV pump device 214A, blood pump 214B, chest compression device 214C, artificial lung 214D, artificial heart 214E or defibrillator 214F to execute or adjust medical procedures (e.g. adjustment of CPR compressions band, adjustment of blood flow pump, adjustment of airflow pump, etc.).

Although the overall operational flow of control system 200 is described above, specific examples for controlling manual/automated CPR and ECLS are described below. It is noted that although the examples below focus on CPR and ECLS applications of the system, other applications are possible (e.g. controlling other types of manual/automated medical procedures based on cerebral tissue parameters, such as artificial hearts, ventricular assist devices, cardiopulmonary bypass systems, and medication delivery, etc.).

CPR Application

Figure 4A:
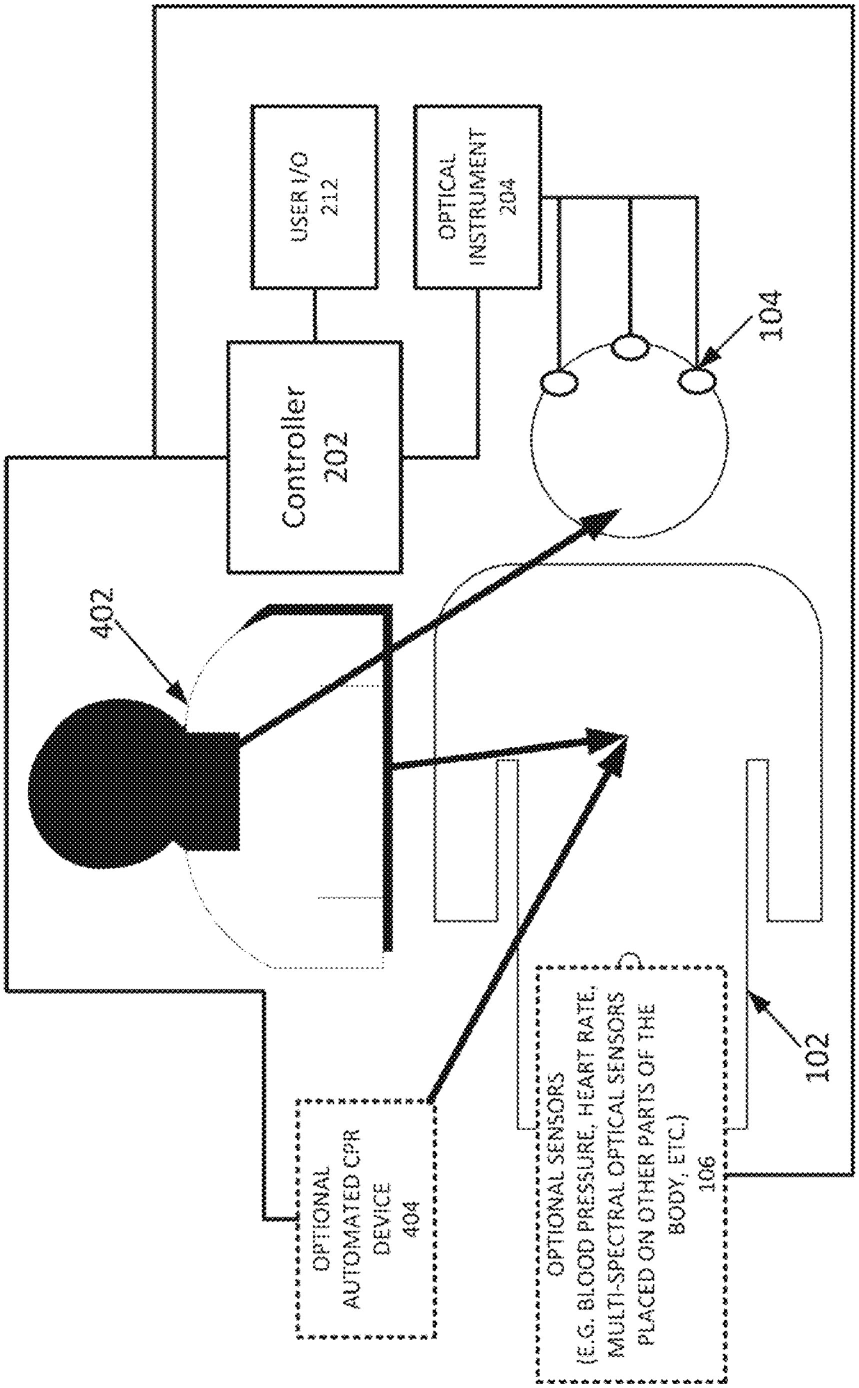
FIG. 4A is a view of a CPR guidance/control system, based on cerebral monitoring according to an aspect of the disclosure.

FIG. 4A is a view of a CPR guidance/control system 400 based on cerebral monitoring. In this example, caregiver 402 is performing CPR on patient 102 with the aid of CPR guidance/control system 400 that includes controller 202, optical instrument 204, measurement probes 104, user I/O 212, and optional sensors 106 (e.g. blood pressure, peripheral blood flow (including carotid blood flow), heart rate, optical measurement probes positioned on other parts of the body (carotid, heart, arms, legs, etc.)). In one example, CPR is manually performed by caregiver 402. In another example, CPR is automatically performed by optional automated CPR device 404 (e.g. including chest-compressing piston, artificial lung, etc.) under the supervision of caregiver 402.

Figure 4B:
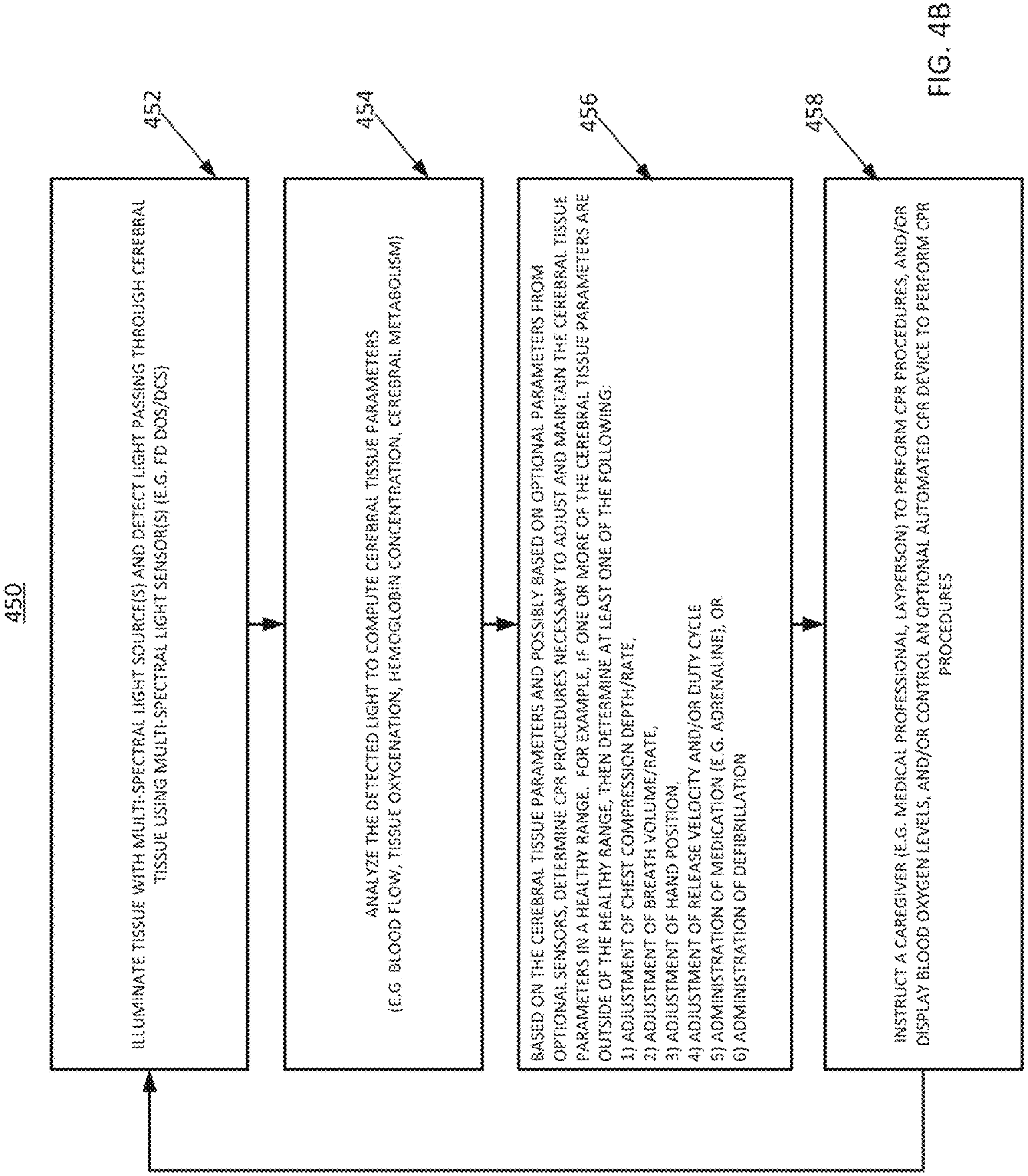
FIG. 4B is a flowchart for the CPR guidance/control system, shown in FIG. 4B, according to an aspect of the disclosure.

FIG. 4B is a view of a flowchart 450 for the operation of the CPR guidance/control system 400 shown in FIG. 4A. In step 452, CPU 202A of controller 202 executes a computer program stored in memory 202B. The computer program instructs CPU 202A to control optical instrument 204 to illuminate the tissue 216 (e.g. cerebral tissue) of patient 102 with RF modulated light (e.g. multi-spectral light) via one or more optical emitters 208 and to detect light passing through tissue 216 (e.g. cerebral tissue) via one or more optical detectors 210.

In one example, CPU 202A may control multiplexer 204(B) to perform time division multiplexing to sequentially output lasers 204(A), each having unique wavelengths and each driven by RF modulator 204C which amplitude modulates the lasers onto an RF optical carrier (e.g. 110 MHz), which then outputs the modulated light to one or more optical emitters 208 for a period of time T. In step 454, the light detected by one or more optical detectors 210 and detectors 204D is then analyzed by CPU 202A to compute the cerebral tissue parameters of interest. More specifically, steps 452 and 454 may utilized the FD-DOS/DCS methods as described above.

Based on the cerebral tissue parameters determined in step 454, and possibly based on optional parameters from optional sensors 106 and optional patient information input via user I/O 212, CPU 202A, in step 456 determines manual CPR procedures or automatic CPR procedures (e.g. adjustment of chest compression depth/rate, adjustment of breath volume/rate, adjustment of hand position, adjustment of chest compression duty cycle, administration of medication, administration of defibrillation, etc.) that are beneficial in adjusting and maintaining the cerebral tissue parameters in a healthy range. CPU 202A determines the appropriate adjustments of these procedures based on a predetermined table of CPR procedures that are associated with certain cerebral tissue parameters, or based on an algorithm that computes (e.g. in real-time) which CPR procedures should be adjusted, such as compression quality, device and hand position, ventilation rates, oxygen delivery, medication delivery and timing, when to activate ECLS, when to discontinue support, etc. The predetermined table and/or the algorithm for determining the CPR procedures to execute based on the cerebral tissue parameters may be based on medical research and optional patient information input to controller 200 via user I/O 212. For example, although not necessary, the caregiver may input the patient's age, weight, etc. into controller 200 via user I/O 212. Controller 200 may then access the predetermined table and/or adjust the algorithm based on this information (e.g. patient information may have an influence on the type and the adjustment of the CPR procedures). Alternatively, the caregiver may determine the manual CPR procedures or automatic CPR procedures based on an analysis of the cerebral tissue parameters, the optional parameters, the optional patient information input, professional experience and other factors.

In step 458, CPU 202A then: 1) instructs caregiver 402 via one or more of display 212B, haptic feedback device 212C, speaker 212D, virtual reality device 212E or indicator lights 212F to execute/adjust the determined CPR procedure, and/or 2) displays blood oxygen levels, and/or 3) controls automated CPR device 404 to execute/adjust the determined CPR procedure.

ECLS Application

Figure 5A:
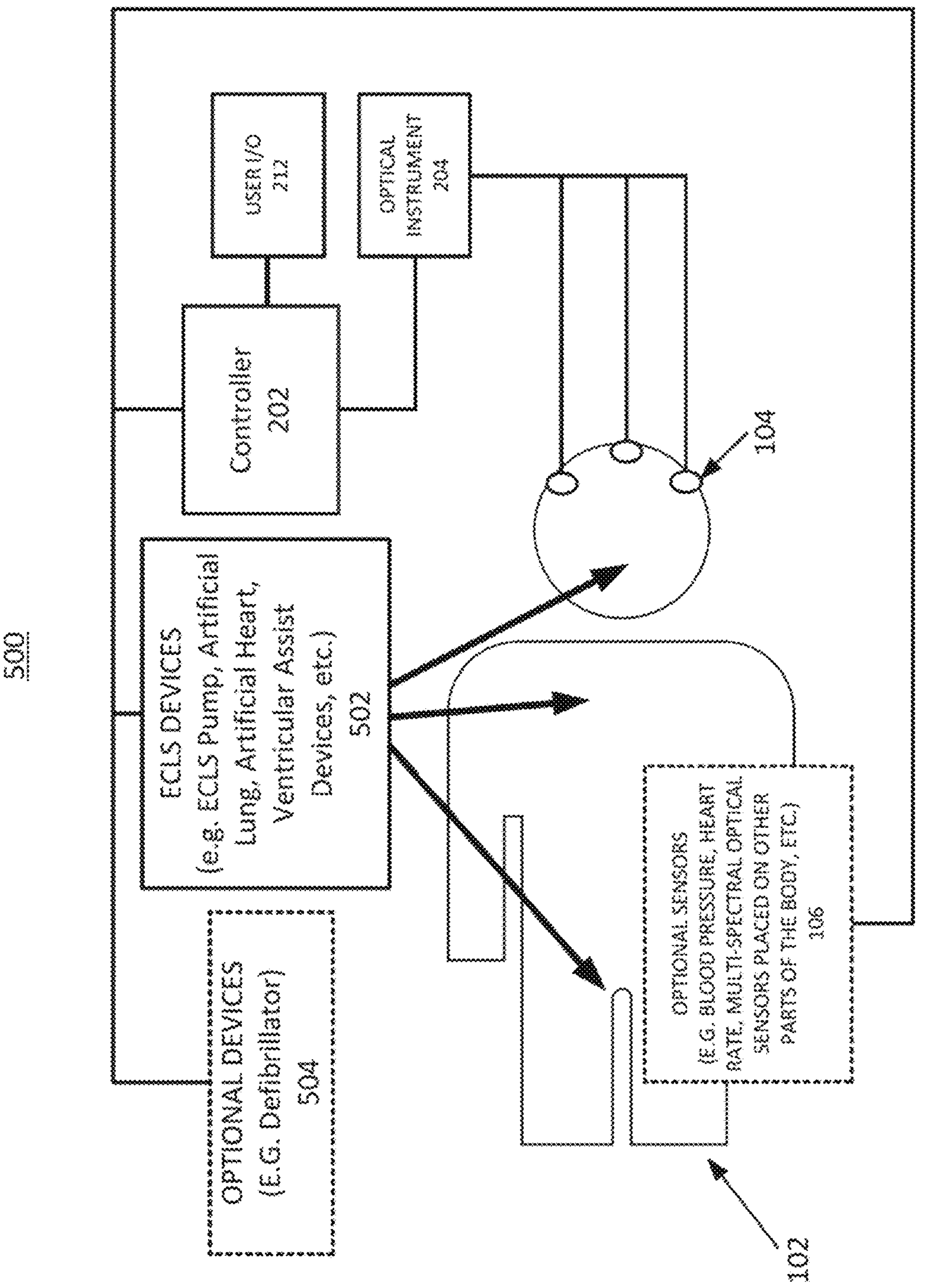
FIG. 5A is a view of an ECLS guidance/control system, based on cerebral monitoring according to an aspect of the disclosure.

FIG. 5A is a view of a guidance/control system 500 for controlling ECLS based on cerebral monitoring. In this example, ECLS guidance/control system 500 is performing ECLS on patient 102. ECLS guidance/control system 500 includes controller 202, user I/O 212, measurement probes 104, optical instrument 204, ECLS devices 502 (e.g. ECLS Pump, artificial lung, artificial heart, ventricular assist devices, etc.), optional sensors 106 (e.g. blood pressure, peripheral blood flow (including carotid blood flow), heart rate, optical measurement probes positioned on other parts of the body (carotid, heart, arms, legs, etc.)) and other optional devices 504 (e.g. defibrillator). In general, ECLS is automatically performed by automated ECLS devices 502 which are controlled by controller 202.

Figure 5B:
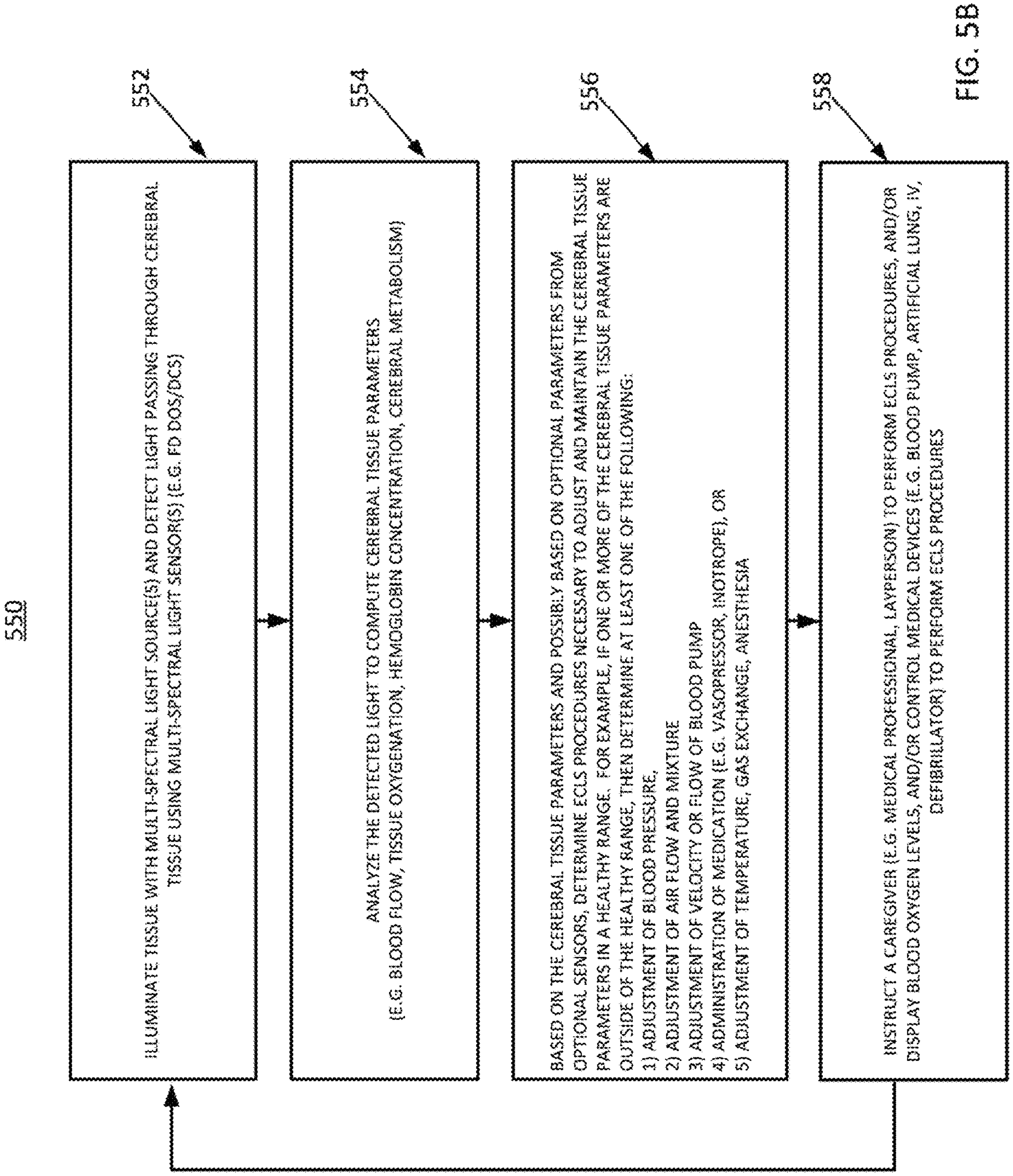
FIG. 5B is a flowchart for the ECLS guidance/control system, shown in FIG. 5A, according to an aspect of the disclosure.

FIG. 5B is a flowchart 550 for the operation of the ECLS guidance/control system 500 shown in FIG. 5A. In step 552, CPU 202A of controller 202 executes a computer program stored in memory 202B. The computer program instructs CPU 202A to control optical instrument 204 to illuminate the tissue 216 (e.g. cerebral tissue) of patient 102 with light (e.g. multi-spectral light) via one or more optical emitters 208 and to detect light passing through tissue 216 (e.g. cerebral tissue) via one or more optical detectors 210.

Similar to the CPR application described above, CPU 202A may control multiplexer 204B to perform time division multiplexing to sequentially output lasers 204A, having unique wavelengths and driven by RF modulator 204C which optically modulates the lasers onto an RF optical carrier (e.g. 110 MHz), which then sequentially outputs the modulated light to one or more optical emitters 208 for a period of time T. In step 554, the detected light is then analyzed by CPU 202A to compute the cerebral tissue parameters, which (similar to the CPR application described above) include but are not limited to optical absorption and optical scattering, blood flow, tissue oxygenation, hemoglobin concentration and cerebral metabolism. More specifically, steps 552 and 554 may also include FD-DOS/DCS methods and other diffuse reflectance spectroscopy methods as described above.

Based on the cerebral tissue parameters determined in step 554, and possibly based on optional parameters from optional sensors 106 and optional patient information input via user I/O 212, CPU 202A, in step 556 controls adjustment of automatic ECLS procedures (e.g. adjustment of blood flow, gas flow, core or brain temperature, administration of medication, etc.) to adjust and maintain the cerebral tissue parameters in a healthy range. CPU 202A makes this determination based on a predetermined table of ECLS procedures that are associated with certain cerebral tissue parameters, or based on an algorithm that computes (e.g. in real-time) which ECLS procedures should be adjusted, examples include, alterations in mechanical blood flow, oxygen delivery, carbon dioxide removal, changes in core or brain temperature, medication delivery and timing, blood product administration, early warning device for cerebral injury, etc. The predetermined table and/or the algorithm for determining the ECLS procedures to execute based on the cerebral tissue parameters may be based on medical research and optional patient information input to controller 200 via user I/O 212. For example, although not necessary, the caregiver may input the patient's age, weight, etc. into controller 200 via user I/O 212. Controller 200 may then access the predetermined table and/or adjust the algorithm based on this information (e.g. patient information may have an influence on the type and the adjustment of the ECLS procedures). Alternatively, the caregiver may determine the adjustments of automatic ECLS procedures based on an analysis of the cerebral tissue parameters, the optional parameters, the optional patient information input, professional experience and other factors.

In step 558, CPU 202A then: 1) instructs caregiver 402 via one or more of display 212B, haptic feedback device 212C, speaker 212D, virtual reality device 212E or indicator lights 212F to execute/adjust the determined ECLS procedures, and/or 2) displays blood oxygen levels, and/or 3) controls automated ECLS devices 502 to execute/adjust the determined ECLS procedures.

Switching from CPR to ECLS

As described with respect to FIGS. 4A, 4B, 5A and 5B, the medical procedure systems 400 and 500 are able to suggest manual adjustment of CPR or ECLS procedures and control automated adjustments of CPR or ECLS procedures. In some cases, when performing CPR, however, it may also be beneficial to determine when to switch from CPR to ECLS.

Figure 6:
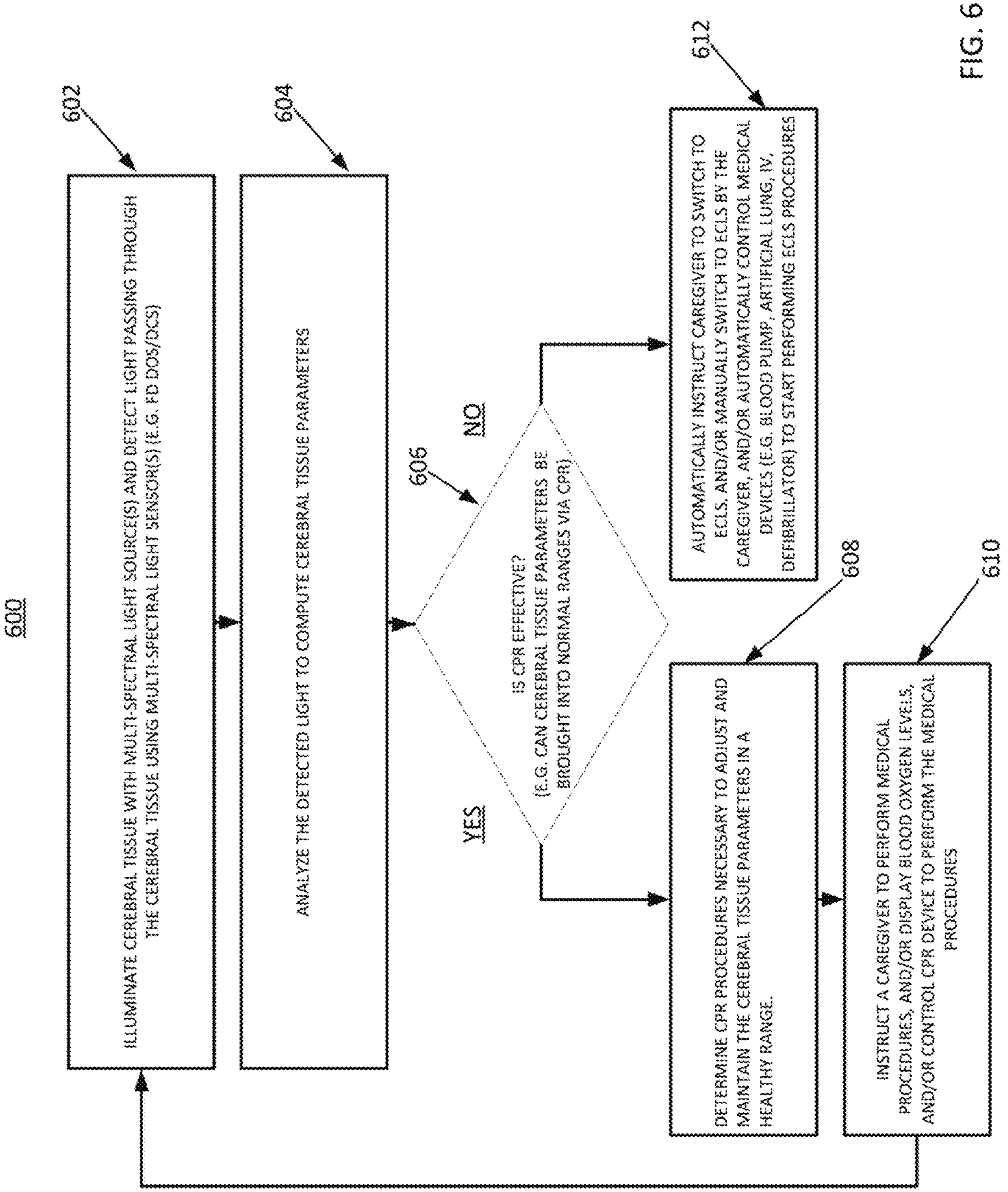
FIG. 6 is a flowchart for switching between CPR and ECLS, according to an aspect of the disclosure.

FIG. 6 is flowchart 600 for switching between CPR and ECLS. In step 602, CPU 202A controls optical instrument 204 to illuminate the tissue 216 (e.g. cerebral tissue) of patient 102 with light (e.g. multi-spectral light) via measurement probes 206 and to detect light passing through tissue 216 (e.g. cerebral tissue) via measurement probes 206. In step 604, the detected light is then analyzed by CPU 202A to compute cerebral tissue parameters.

Based on the cerebral tissue parameters (e.g. blood oxygen levels) determined in step 604, and possibly based on optional parameters from optional sensors 106 and optional patient information input via user I/O 212, CPU 202A or the caregiver, in step 606 determines if CPR is effective or not. In one example, in step 606, CPU 202A may automatically make this determination based on whether the cerebral tissue parameters and/or optional parameters from optional sensors 106 and/or whether optional patient information are outside of a range where CPR is clinically known to be effective, and/or based on whether the cerebral tissue parameters have improved or not with the administration of CPR. In another example, in step 606, the caregiver may manually make this determination based the cerebral tissue parameters (e.g. displayed blood oxygen levels) and/or the optional parameters from optional sensors 106 and/or whether the optional patient information are outside of a range where CPR is clinically known to be effective, and/or based on whether the cerebral tissue parameters have improved or not with the administration of CPR. This manual/automatic decision can be made at any point during the CPR process.

If CPR is deemed to be effective in step 606, then in step 608, CPU 202A and/or the caregiver determines adjustments of manual CPR procedures and/or automated CPR procedures needed to adjust and maintain the cerebral tissue parameters in a healthy range. In step 610, CPU 202A then: 1) instructs caregiver 402 via one or more of display 212B, haptic feedback device 212C, speaker 212D, virtual reality device 212E or indicator lights 212F to execute/adjust the determined CPR procedure, and/or 2) displays blood oxygen levels, and/or 3) controls automated CPR device 404 to execute/adjust the determined CPR procedure.

If, however, CPR is deemed to be ineffective in step 606 based on cerebral physiologic response to CPR (e.g. the cerebral parameters cannot be brought into the healthy range using CPR), then in step 612, CPU 202A instructs caregiver 402 to switch to ECLS. In response to this instruction, caregiver 402 then connects patient 102 to ECLS devices 502, and system 500 performs the ECLS adjustment algorithm described above in flowchart 550. Alternatively, the caregiver can manually determine whether CPR is ineffective and a switch to ECLS is needed by analyzing the display of blood oxygen levels.

CONCLUSION

The steps in FIGS. 1, 3, 4B, 5B and 6 may be performed by the controller 202 in FIGS. 2A, 2B, 4A and 5A, upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. In one example, data are encrypted when written to memory, which is beneficial for use in any setting where privacy concerns such as protected health information is concerned. Any of the functionality performed by the computer described herein, such as the steps in FIGS. 1, 3, 4B, 5B and 6 may be implemented in software code or instructions which are tangibly stored on a tangible computer readable medium. Upon loading and executing such software code or instructions by the computer, the controller may perform any of the functionality of the computer described herein, including the steps in FIGS. 1, 3, 4B, 5B and 6 described herein.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described specific examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. An extracorporeal life support (ECLS) cerebral monitoring device comprising:

a measurement probe including:
  one or more optical emitters, and
  one or more optical detectors;
an optical instrument including:
  an optical source, and
  an optical detector; and
a controller configured to:
  control the optical instrument to emit multi-spectral light through the one or more optical emitters to illuminate a tissue,
  control the one or more optical detectors of the measurement probe to detect multi-spectral light emitted from the illuminated tissue,
  compare the emitted multi-spectral light to the detected multi-spectral light,
  compute a plurality of cerebral tissue parameters based on the comparison, wherein the plurality of tissue parameters comprises blood flow,
  determine ECLS procedures based on the plurality of cerebral tissue parameters, and
  control a user output device to perform one or both steps of i) instructing a user to perform the ECLS procedures, and ii) controlling an automated ECLS device to perform the ECLS procedures, wherein the user output device comprises a haptic feedback module, and wherein instructions output by the user output device comprise at least one of administration of medication and alteration of anesthesia.

2. The ECLS cerebral monitoring device of claim 1,
wherein the controller is further configured to control the optical source, control the one or more optical detectors of the measurement probe, and compare the emitted multi-spectral light to the detected multi-spectral light according to at least one of frequency-domain diffuse optical spectroscopy (FD-DOS) and diffuse correlation spectroscopy (DCS), or time-domain diffuse optical spectroscopy (TD-DOS) and DCS techniques.

3. The ECLS cerebral monitoring device of claim 1,
wherein the plurality of cerebral tissue parameters further comprises at least one of optical scattering, optical absorption, oxygenation of the tissue, hemoglobin concentration and cerebral metabolism.

4. The ECLS cerebral monitoring device of claim 1,
wherein the user output device further comprises at least one of an audio output and a visual output, and
wherein the instructions output by the user output device further comprise output by at least one of the audio output and the visual output.

5. The ECLS cerebral monitoring device of claim 1,
wherein the automated ECLS device includes at least one of a blood pump, artificial heart, artificial lung and a ventricular assist device, and
wherein the controller is further configured to control the automated ECLS device to adjust at least one of blood pressure, blood flow or blood velocity output by the blood pump, gas flow and mixture output by the artificial lung and medication administration.

6. The ECLS cerebral monitoring device of claim 1, further comprising:
at least one of a blood pressure sensor and a heart rate sensor,
wherein the controller is further configured to control the user output device to instruct the user to perform the ECLS procedures, or control the automated ECLS device to perform the ECLS procedures based on measurements from the at least one of the blood pressure sensor and the heart rate sensor.

7. The ECLS cerebral monitoring device of claim 1, further comprising:
a defibrillator device,
wherein the controller is further configured to control the defibrillator device based on the plurality of cerebral tissue parameters.

8. The ECLS cerebral monitoring device of claim 1,
wherein the optical instrument includes a radio frequency (RF) optical modulator,
wherein the optical source includes plurality of lasers, and wherein the controller is further configured to control the optical instrument to emit multi-spectral light by sequentially inputting the plurality of lasers into the RF optical modulator which modulates the plurality lasers and outputs the modulated lasers through the one or more optical emitters to illuminate the tissue.

* * * * *